United States Patent
Farahbakhshian et al.

(10) Patent No.: US 10,881,325 B2
(45) Date of Patent: Jan. 5, 2021

(54) MOTOR DRIVEN TURNTABLE WITH INTEGRATED ELECTRONIC SCALE

(71) Applicant: NAKED LABS AUSTRIA GMBH, Vienna (AT)

(72) Inventors: Farhad Farahbakhshian, San Jose, CA (US); Peter Kreuzgruber, Vienna (AT)

(73) Assignee: Naked Labs Austria GMBH, Vienna (AT)

( * ) Notice: Subject to any disclaimer, the term of this patent is extended or adjusted under 35 U.S.C. 154(b) by 76 days.

(21) Appl. No.: 16/301,001

(22) PCT Filed: May 12, 2017

(86) PCT No.: PCT/EP2017/061480
§ 371 (c)(1),
(2) Date: Nov. 13, 2018

(87) PCT Pub. No.: WO2017/194747
PCT Pub. Date: Nov. 16, 2017

(65) Prior Publication Data
US 2019/0175069 A1    Jun. 13, 2019

(30) Foreign Application Priority Data
May 12, 2016   (DE) .......... 10 2016 108 857

(51) Int. Cl.
*A61B 5/107*       (2006.01)
*G01G 19/50*       (2006.01)
*G01G 19/44*       (2006.01)

(52) U.S. Cl.
CPC .......... *A61B 5/1073* (2013.01); *A61B 5/1075* (2013.01); *A61B 5/1079* (2013.01); *G01G 19/445* (2013.01); *G01G 19/50* (2013.01)

(58) Field of Classification Search
CPC ... A61B 5/1073; A61B 5/1075; A61B 5/1079; G01G 19/445; G01G 19/50
(Continued)

(56) References Cited

U.S. PATENT DOCUMENTS 4,993,506 A    2/1991  Angel
8,698,637 B2*  4/2014  Raichman ............ G08B 21/245
                                                        340/573.1

(Continued)

FOREIGN PATENT DOCUMENTS

| CN | 104983445 | 10/2015 |
| EP | 1882447   | 1/2008  |
| JP | 2005230160| 9/2005  |

OTHER PUBLICATIONS

International Search Report (PCT/EP2017/061480), dated Aug. 7, 2017.

(Continued)

*Primary Examiner* — Jacques M Saint Surin
(74) *Attorney, Agent, or Firm* — Dority & Manning, P.A.

(57) ABSTRACT

The invention relates to a motor driven turntable for a personal biofeedback apparatus and/or a medical diagnostic apparatus. The motor driven turntable includes a bottom plate, a rotatable top plate, a motor for driving the top plate, an integrated electronic scale for measuring the weight of a person positioned on the top plate and a wireless interface that permits communication between the scale and an external computer of the personal biofeedback apparatus and/or medical diagnostic apparatus.

8 Claims, 5 Drawing Sheets

(58) Field of Classification Search
USPC .................................................... 177/25.13
See application file for complete search history.

(56) References Cited

U.S. PATENT DOCUMENTS

| | | | | |
|---|---|---|---|---|
| 2002/0178830 | A1* | 12/2002 | Kazerooni | ............. B65G 43/00 |
| | | | | 73/760 |
| 2012/0212344 | A1* | 8/2012 | Forsberg | ................. G08B 3/10 |
| | | | | 340/573.1 |
| 2014/0266692 | A1* | 9/2014 | Freedman | ............ G08B 21/245 |
| | | | | 340/539.11 |

OTHER PUBLICATIONS

Naked Labs: Naked Labs Unveils World's First 3D Fitness Tracker, Apr. 4, 2016, retrieved from the Internet: URL:http://prnewswire.com/news-releases/naked-labs-unveils-worlds-first-3d-fitness-tracker-300251292.html.

* cited by examiner

MOTOR DRIVEN TURNTABLE WITH INTEGRATED ELECTRONIC SCALE

FIELD OF THE INVENTION

The invention relates to a motor driven turntable for at least one of fitness monitoring, personal biofeedback and medical diagnostic apparatus and includes an integrated electronic scale for measuring the weight of a person positioned on the turntable. Furthermore, the turntable can form an arrangement with an apparatus for optical measurement of a body of the inspected person with a computer.

BACKGROUND OF THE INVENTION

From the EP 1 882 447 A1 an anthropometric unit is known, having means for the determination of body volume (BV) of the subject to be measured selected from the group consisting of optical means, ultrasound means and structured light systems; a bioimpedance system; a system for measuring body weight; a control system and data elaboration unit. The combination of an anthropometric unit and of a bioimpedance system provides reliable measures and the correct determination of the parameters of interest, in particular body volume and body fat. The correct determination of these parameters allows the use of the device of the present invention in the medical field, in particular a correct determination in morbidly obese subjects. For example, the support, such as a platform, where the subject stands up can rotate while the vertical axis, where the sensor system is positioned, does not rotate. The body weight is measured by a scale suitably positioned at the basis of the device to form a common system. The subject to be measured stands on the scale, which can constitute the platform or be integrated in the platform.

BRIEF OBJECTS AND SUMMARY OF THE INVENTION

According to the disclosure, a motor driven turntable for at least one of fitness monitoring, personal biofeedback and medical diagnostic apparatus is suggested. The motor driven turntable comprises a bottom plate, a rotatable top plate, a motor for driving the top plate, an integrated electronic scale for measuring the weight of a person positioned on the top plate and a wireless interface to communicate with an external computer of the fitness monitoring, personal biofeedback and/or medical diagnostic apparatus.

It is advantageous if the wireless interface is a WLAN, WIFI, Zigbee and/or Bluetooth interface.

In an advantageous further aspect, the motor driven turntable comprises an electronic module, in particular an electronic circuitry and/or a microprocessor. The electronic module controls the turning speed and/or the position of the top plate. Additionally or alternatively, the electronic module controls a power supply unit, in particular a rechargeable battery.

It is advantageous if the motor driven turntable comprises a, in particular optical and/or magnetic, position detection unit for measurement of an angular position of the top plate.

In an advantageous further aspect, the position detection unit comprises an optical and/or magnetic sensor.

It is advantageous if the electronic module is for interpreting and analyzing data, in particular of the integrated electronic scale and/or of the optical and/or magnetic sensor, and/or for control of the motor.

In an advantageous further aspect, the wireless interface provides the acquired data from the electronic module to the external computer and/or supplies data of the angular position of the top plate and/or of the person's weight to the external computer.

It is advantageous if the wireless interface allows the external computer to control the turntable, in particular the motor.

In an advantageous further aspect, the motor driven turntable comprises a power supply unit, in particular a rechargeable battery, to provide electrical power for the motor and the electronic module.

Further, according to the disclosure, an arrangement for at least one of fitness monitoring, personal biofeedback and medical diagnostic of a person is suggested. The arrangement comprises an apparatus for optical measurement of a body of the inspected person. The apparatus comprises a computer. Further, the arrangement comprises a motor driven turntable in accordance with the previous specification. The motor driven turntable comprises a bottom plate, a rotatable top plate, a motor for driving the top plate, an integrated electronic scale for measuring the weight of the person positioned on the top plate and a first wireless interface to communicate with the external computer of the apparatus.

It is advantageous if the computer comprises a second wireless interface, which is wireless connected to the first wireless interface.

It is advantageous if the computer comprises a third wireless interface for connecting the computer to a smartphone.

In an advantageous further aspect, the apparatus is a 3D body scanner and/or comprises at least one color camera, depth sensor and/or far infrared temperature sensor.

Further, the invention relates in particular to a microprocessor controlled and motor driven turntable with integrated scale, particularly for use in fitness monitoring, personal biofeedback or medical diagnostic apparatus. The turntable is composed of a chassis in which the scale sensors are mounted, a sensor plate carrying support rollers and/or the driving unit, and/or a rigid top plate.

The invention relates to a motor driven turntable with integrated electronic scale for use in fitness monitoring, biofeedback or medical diagnostic apparatus for persons, in which data of weight and rotation angle of the turntable are supplied on a wireless computer interface, eg. MAN, WIFI, Zigbee and/or Bluetooth, and in which the rotation of the turntable is under control of an external computer.

Turntables for various objects used in photography as object supports frequently use a single central shaft that carries and drives the object supporting plate, therefore a heavy construction is needed to mount the shaft.

Medical diagnostics, fitness monitoring and/or biofeedback apparatus require various data of the inspected person, e.g. weight, size of body, body structure, etc. Some of these parameters are refined from photographical, optical and/or microwave measurement, requiring that the person is rotated around the vertical axis during inspection process. This rotation is conducted by an electronic module—in particular a microcontroller—operated and/or motor driven turntable with integrated electronic scale. The motor driven turntable measures the weight of the person and supplies data of the weight and/or of the rotation angle of the top plate to a computer for parameter analysis. In particular, the motor driven turntable with integrated electronic scale of the invention comprises:

(a) a rigid, motor driven top plate, withstanding the weight of a person standing or an object lying on the turntable, with a driving shaft mounted to the bottom side, whereby the directions of the symmetry axes of top plate and shaft are coincident;

(b) a chassis acting as bottom plate and lower part of the housing comprising:

load cells firmly mounted to the bottom plate within the chassis, (ii) at least one sensor plate, resting on and fixed to load cells, so that each of the sensor plates is firmly connected to but not in touch with the chassis, (iii) vertical supporting rollers—in particular ball bearings—resting in a guideway or fixed on a sensor plate, so that the positions of the pitch points of the wheels touching the top plate are exactly above the load cells respectively, so that the direction of the flux of force is exactly vertical and no bending moment applies to the sensor plates, (iv) a gear, mounted to a sensor plate, to apply the driving torque to the driving shaft of the top plate, comprising driving and driven wheels as well as bearings for supporting vertical and horizontal load as applied from the top plate if the turntable is not standing exactly leveled, and to support the top plate in the center, (v) a motor, mounted to a sensor plate, to provide the driving torque via a coupling to the gear, (vi) electronic module, in particular an electronic circuitry and/or microprocessor, for interpreting and analyzing data of scale sensors and/or for control of the motor, in particular of the speed, position and/or torque of the motor, and (vii) a power supply unit, in particular a rechargeable battery, to provide electrical power for motor and electronic circuitry; and (c) nonslip feet on the bottom side of the chassis below each load cell and in the axis of the flux of force.

Furthermore, a position detection unit, in particular with an optical or a magnetical sensor or both, is included within the chassis of the turntable for measurement of the angular position. A wireless interface is also included, which allows an external computer to control the turntable and which provides acquired data from the microprocessor within the turntable to the external computer.

The turntable of the present invention is designed to allow low cost production, as the flux of force is vertical and therefore only the top plate needs to be rigid enough to carry the whole load of the object.

DETAILED DESCRIPTION

Figure 1A:
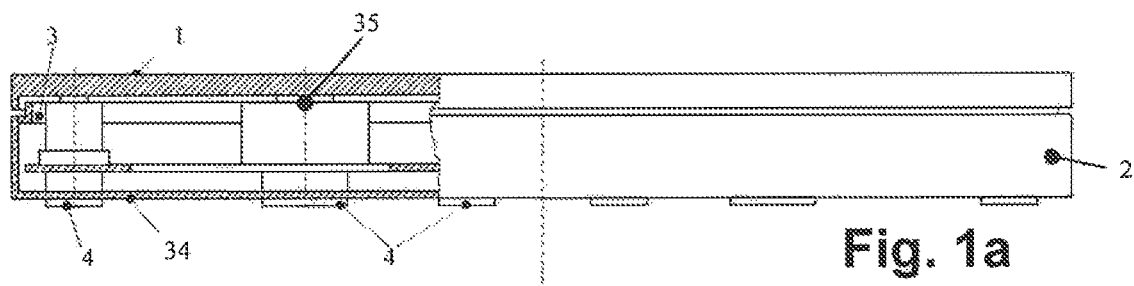
FIG. 1a is a side view and FIG. 1b is a top plan view, with partial cutaways, of the embodiment of a motor driven turntable with integrated electronic scale in accordance with the present invention.
Figure 1B:
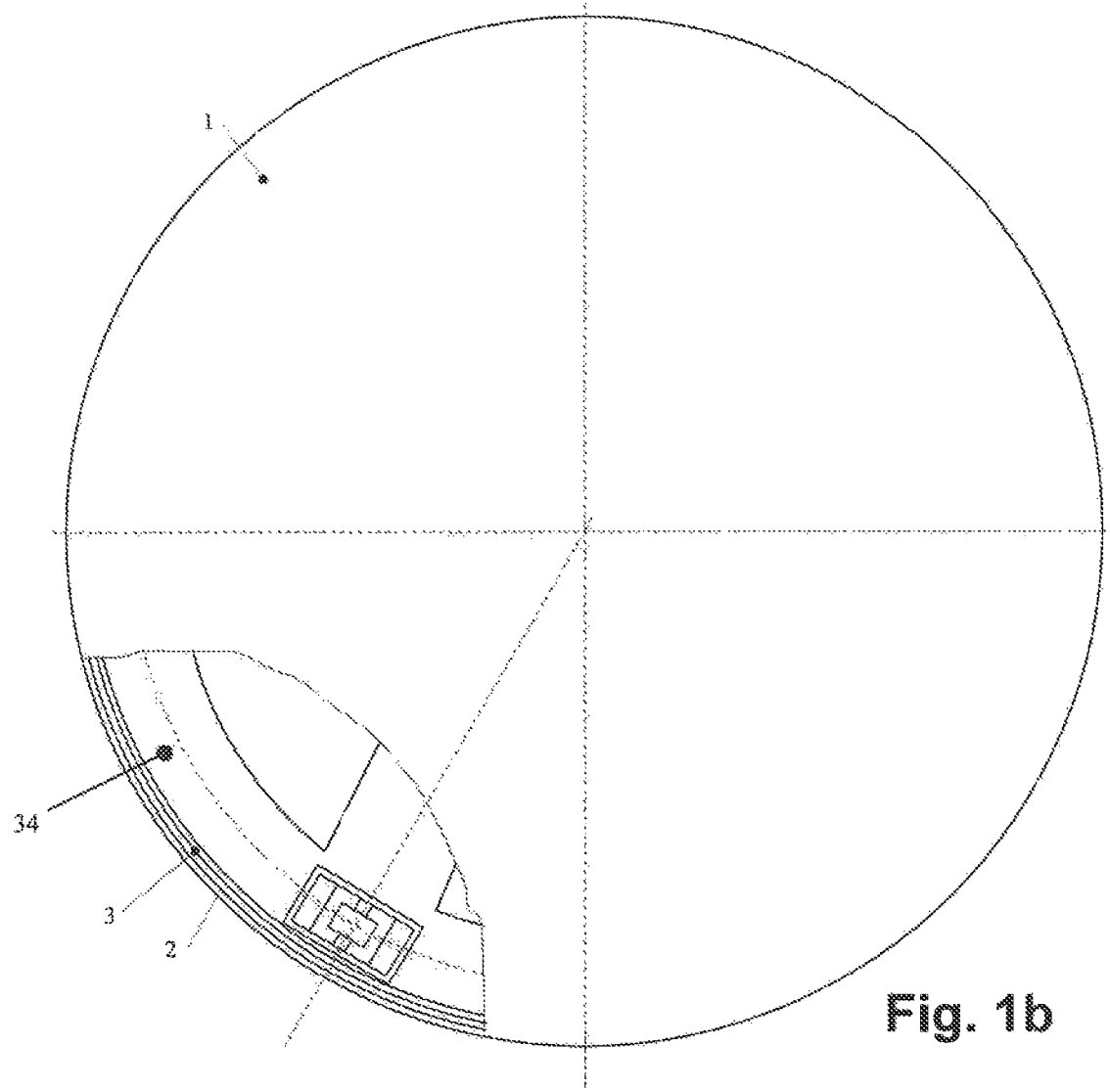

FIGS. 1a and 1b show the external and partially cross-sectional view of the embodiment of a motor driven turntable with integrated electronic scale 35 of the present invention. The top plate 1 of the turntable is of rigid construction with the purpose to carry the load applied to the turntable and distribute the bearing-strength to the subjacent supports. A cylindrical skirt at the framing of the top plate contributes to the appearance of the turntable. The top plate can be made of homogeneous metal, wood, glass, marble, plastics, a compound of several materials, or any other material that is rigid enough to carry the load. To achieve an acceptable surface, the top table might be coated or painted.

The chassis 2 forms the main part of the housing of the turntable as it contains all parts and subassemblies. Therefore, apertures, screw holes, tapped bushings, pods, fixing clips, cable fasteners, and other devices for clamping and fixing subassemblies, modules and cables might also be part of the chassis as ribs for strengthening the stability. As the chassis might be made of punched steel, metal die casting, or molded plastics, the surface will also be coated or painted.

A ring-shaped frame 3 with attached skirt of cylindrical shape, is put on the chassis or top plate to clad the gap between chassis and top plate. The whole turntable rests on nonslip feet 4 that will also serve as compensation of surface irregularities of the floor.

Figure 2A:
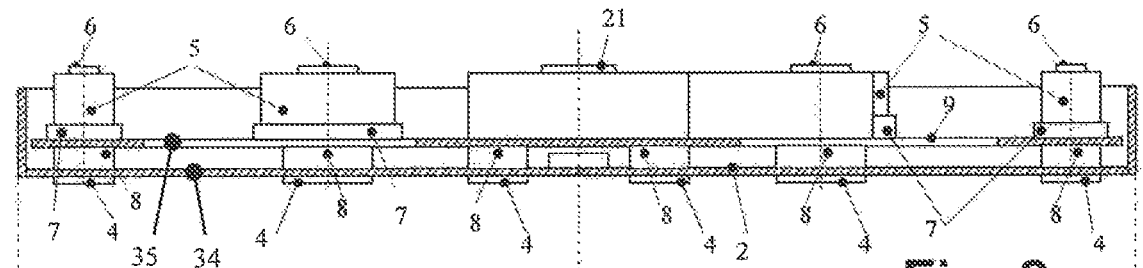
FIG. 2a is a cross-sectional view and FIG. 2b is a top plan view of the one embodiment of the turntable with removed top plate and frame.
Figure 2B:
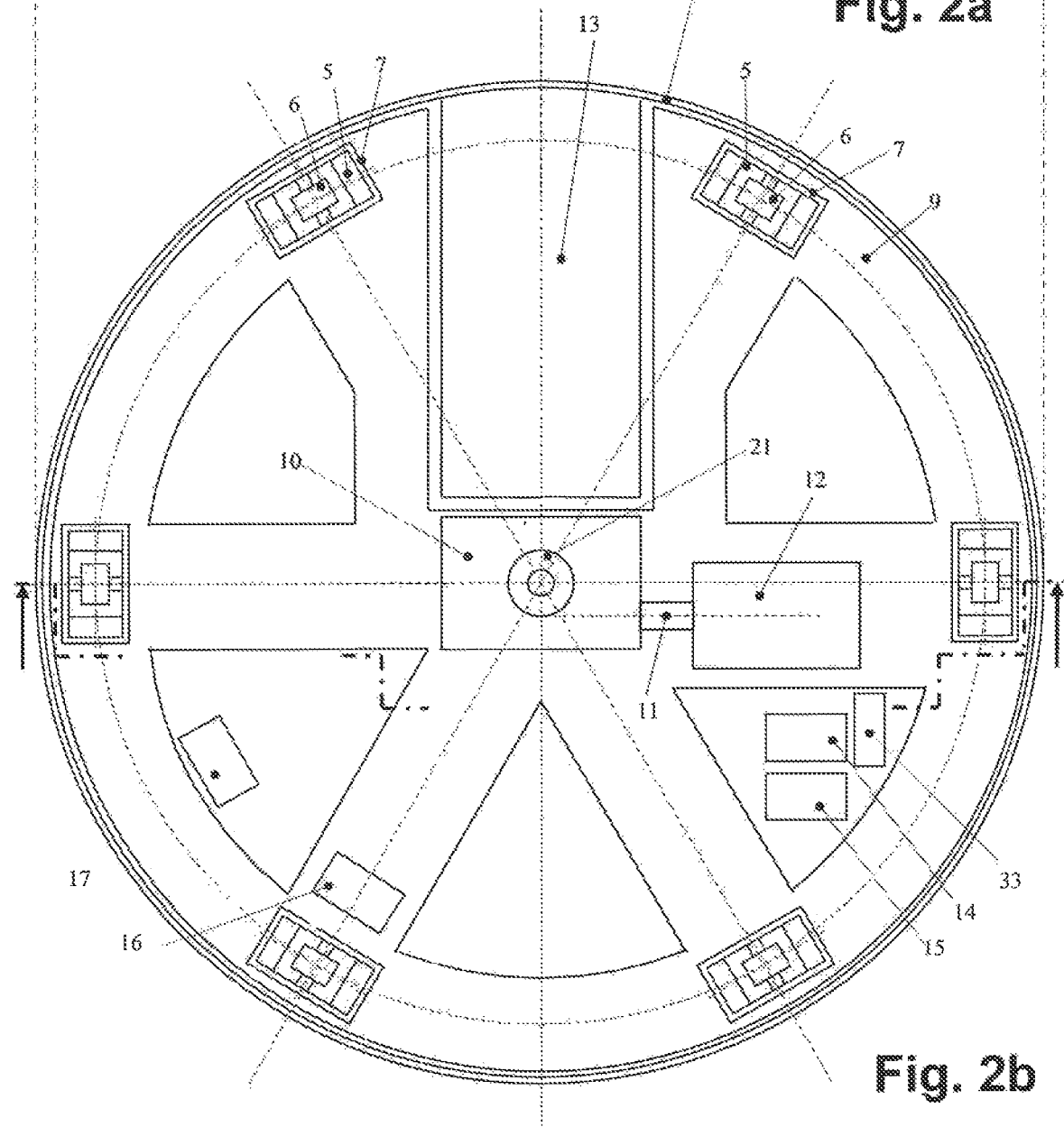

FIGS. 2a and 2b show the internal and partially cross-sectional view of the preferred embodiment of the invention, where top plate 1 and ring-shaped frame 3 are removed for the depiction. The motor driven turntable for at least one of personal fitness monitoring, biofeedback and medical diagnostic apparatus comprises a bottom plate 34, the rotatable top plate 1 (FIGS. 1a and 1b), a motor 12 (FIG. 2b) for driving the top plate 1, the integrated electronic scale 35 for measuring the weight of a person positioned on the top plate 1 and a wireless interface 33 (FIG. 2b) to communicate with a not shown external computer of the fitness monitoring, personal biofeedback and/or medical diagnostic apparatus. It is advantageous if the wireless interface 33 is a WLAN, WIFI, Zigbee and/or Bluetooth interface. As shown in FIG. 2b, the motor driven turntable comprises an electronic module 14, in particular an electronic circuitry and/or a microprocessor.

The motor driven turntable comprises a, in particular optical and/or magnetic, position detection unit 16, 17 for measurement of an angular position of the top plate 1, The position detection unit 16, 17 comprises an optical and/or magnetic sensor. The electronic module 14 is for interpreting and analyzing data, in particular of the integrated electronic scale 35 and/or of the optical and/or magnetic sensor, and/or for control of the motor 12. The wireless interface 33 provides the acquired data from the electronic module 14 to the external computer, which is not shown in the figures. The wireless interface 33 supplies data of the angular position of the top plate 1 and/or of the person's weight to the external computer. The wireless interface 33 allows the external computer to control the turntable, in particular the motor 12. The top plate 1 can be turned controlled by the external computer in both turning directions. The motor driven turntable comprises a power supply unit 15, in particular a rechargeable battery, to provide electrical power for the motor 12 and the electronic module 14.

Vertical supports 5 carry the top plate 1 and conduct the applied load via one or more sensor plates 9 to the load cells 8. The load cells are fixed within chassis 2 at the bottom plate 34. The nonslip feet 4, mounted to the outside of the chassis, are located at the same horizontal positions as the load cells are fixed inside. Hence, the flux of force is in pure vertical direction from vertical supports to nonslip feet, as long as no thrust in horizontal direction is applied to the top plate.

As vertical supports 5 need a stable position even if thrust in horizontal direction occurs, they are mounted to the sensor plates 9 that are fixed to, but not in touch with, the chassis 2. It is preferable to use only one sensor plate 9 that rests on all load cells 8, as this allows the best distribution of horizontal thrust to the load cells 8. However, constructive requirements may cause to split the sensor plate 9 into two or more parts.

To allow rotation of the top plate 1 around the vertical symmetry axis of the turntable, vertical supports 5 use a roller 6 and/or ball bearing on top that is mounted to a horizontal or nearly horizontal axis within the corpus of the vertical support 5. If the vertical supports 5 are arranged in a circle in the outer region of the turntable, if thrust applied to the top plate 1 perpendicular to the vertical axis is low and/or if the length of the roller 6 and/or ball bearing is small compared to the distance from vertical support 5 to central axis of the turntable, then a cylindrical shape of the support roller 6 and/or ball bearing will suffice. If the extension of the roller 6 and/or ball bearing cannot be neglected, a roller and/or ball bearing of conical shape can be used, but this implies that either the axis of the roller 6 and/or ball bearing is no longer exactly horizontal, or the lower side of the top plate 1 must be conical, at least at the position where the rollers 6 and/or ball bearings will meet the top plate 1. As an alternative, rollers and/or ball bearings shaped as a spherical segment are applied instead of cylindrical ones.

Although it is possible to fix the vertical support 5 directly to a sensor plate 9 with screws, clips, glue, or something else, the preferred embodiment employs a vertical guideway 7 that allows the vertical support 5 to slide in vertical direction. So, if the vertical support 5 rests in its guideway 7 on a spring, e.g. a flat spring, the roller 6 and/or ball bearing will always be pressed to the top plate 1, even if the bottom plate 34 of chassis 2 and therefore the sensor plate 9 will be deformed due to irregularities of the floor.

The preferred embodiment of this invention employs load cells as described in literature, e.g. in U.S. Pat. No. 4,993,506, which patent is hereby incorporated herein in its entirety by this reference for all purposes. Beside the required measure of sensitivity and precision it is only important that the sensors can be fixed on two sides: at the bottom to the chassis 2, and on top to the sensor plate 9.

The number of vertical supports 5 actually used depends on size and application of the turntable. For geometric reasons there shall be at least three of them.

Besides of the vertical supports 5, also modules and subassemblies that shall rest on the load cells 8, e.g. gear 10, motor 12, and magnetic position detection unit 16, will be mounted to a sensor plate 9. Usually a single sensor plate 9 is used to carry all vertical supports 5 and modules, but one that has cut-outs for modules and subassemblies that are mounted to the chassis, e.g. electronic module 14, power supply unit 15, optical position detection unit 17, and space for module plug-ins 13. However, splitting the sensor plate 9 into several parts might also be adequate in some applications. It is useful for a sensor calibration process if the rigidity of each of the several sensor plates 9 is just as high as required for carrying the modules mounted thereto, and the strength required to carry the thrust. Although the sensor plate 9 needs not be of flat design and may even have ribs to increase stiffness.

In the simplest case, the optical position detection unit 17 is a photoelectric barrier, which consists of a light emitting diode and a photoelectric element, e.g. a photo transistor. A top plate 1 that is white at the bottom side, but has one black spot at exactly the same distance from the main symmetry axis as the light emitting diode and the photoelectric element, is one example of an optical marking system that can be used for finding the angular position. Thus, when the top plate 1 rotates, every time the black spot passes the path of the photoelectric barrier, it will be detected. Of course, any combination of colours can be used, as long as the contrast is good enough to trigger the photoelectric barrier. A higher precision in angular resolution can be achieved by arranging more photoelectric barriers side by side, and using a complex angular coding rather than a single spot on the top table.

The magnetic position detection unit 16 requires a single magnetic strip or a coded system of magnetic strips applied on the bottom side of the top plate 1. Thus, a magnetic flux detector can respond, every time the magnetic strip passes the detector.

According to FIG. 2b the motor driven turntable for at least one of personal fitness monitoring, biofeedback and medical diagnostic apparatus comprises the bottom plate 34, the rotatable top plate 1, the motor 12 for driving the top plate 1, the integrated electronic scale 35 for measuring the weight of a person positioned on the top plate 1 and a wireless interface 33 to communicate with an external computer. The external computer is an integral part of the fitness monitoring, personal biofeedback and/or medical diagnostic apparatus. It comprises a second wireless interface, which is wirelessly connected to the first wireless interface 33 of the motor driven turntable.

Figure 3:
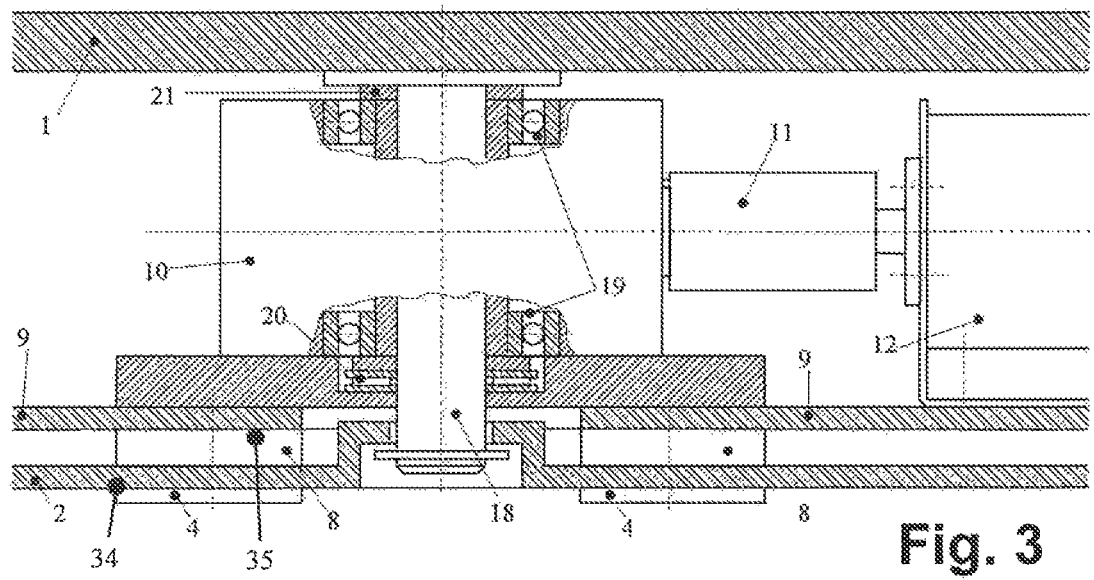
FIG. 3 is a detail of a cross-sectional view of a preferred embodiment of the driving unit.

FIG. 3 shows a cross-sectional view of the preferred embodiment of the driving unit. The main shaft 18 is mounted directly to the top plate 1 on one side, and secured by a retaining ring on the other side. Thus, the main shaft 18 holds the turntable together. A motor 12 drives the main shaft 18 via a coupling 11 and a gear 10, and therefore the top plate 1. Horizontal thrust applied to the top plate 1 is passed to the sensor plate 9 via roller bearings 19 and the housing of the gear 10.

In the preferred embodiment of the invention, the top plate 1 is also supported in the center, additional to the vertical supports on the fringe. For this, a spacer washer 21 transfers a part of the load applied to the turntable from the top plate 1 to the quill of the gear 10, and via an axial roller bearing 20 to the sensor plate 9 and to two or more load cells 8 in the neighborhood of the main shaft 18. If the axial roller bearing is not part of the gear 10, or if the housing of the gear 10 is too small, a rigid support plate might take this task. The thickness of spacer washer 21 defines the partition of load from top plate 1 to vertical supports 5 and main shaft support.

Figure 4:
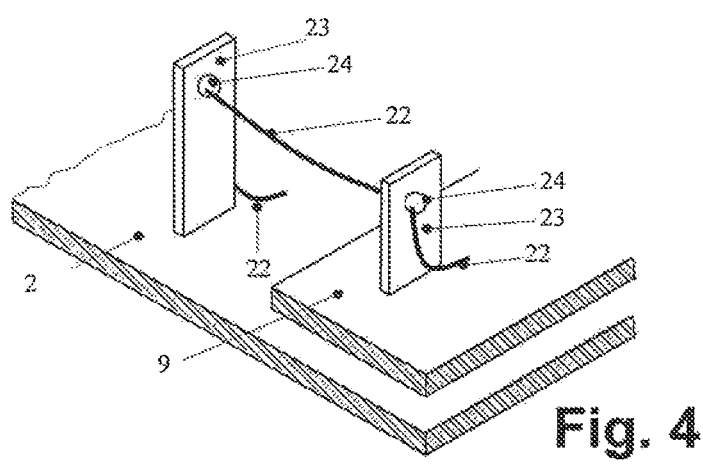
FIG. 4 is a detail of a preferred embodiment of a cable guide from sensor plate to chassis.

FIG. 4 shows the transition of a cable 22 from sensor plate 9 to chassis 2 in such a way that as little as possible of the load from the top plate 1 shall be leaked via stiffness of the cable 22. For this, the cable 22 is guided nearly horizontally over pairs of pillars 23, each one on the sensor plate 9 and one at the bottom of the chassis 2. If the pillars 23 are in some distance from each other, the bending force of the cable 22 and therefore the induced measurement error is small. Each pillar 23 has a widget to fix the cable at that position 24. In the preferred embodiment, the fixation is provided by guiding the cable 22 through a hole in the pillar 23 and plugging the hole with a stopper made of elastic material.

Figure 5:
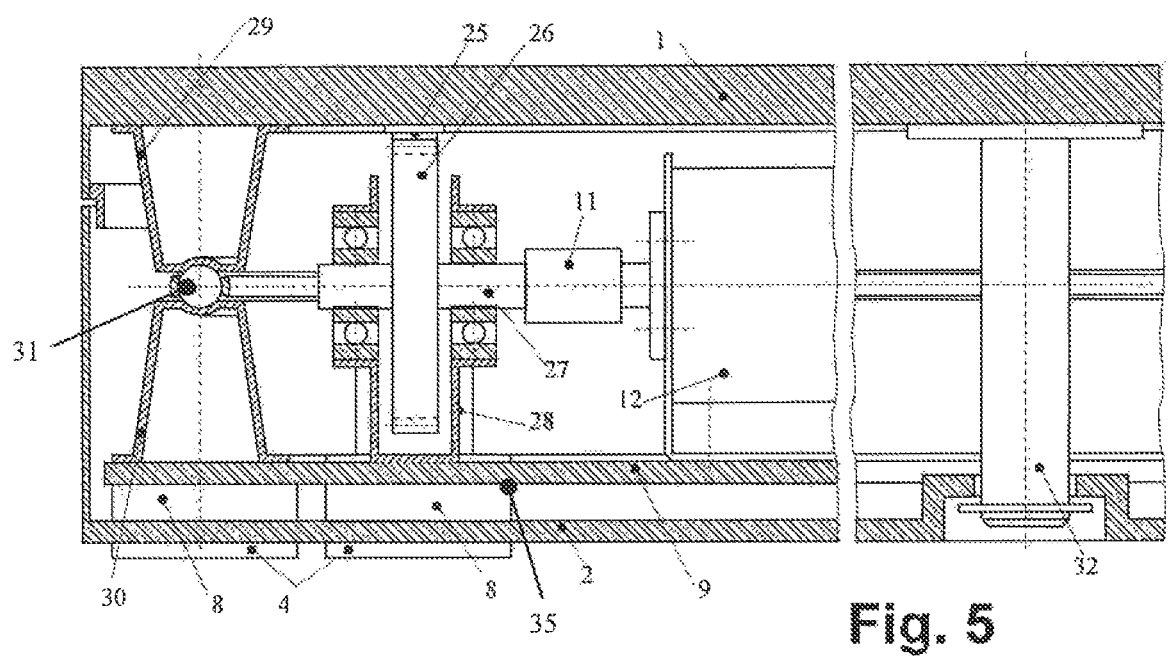
FIG. 5 is a cross sectional view of driving and bearing of the top plate in an alternative embodiment.

FIG. 5 shows a cross-sectional view of driving and bearing of the top plate 1 in an alternative embodiment of the turntable. The top plate 1 is driven by use of a hypoid or bevel gear with a toothed ring 25 mounted directly to the bottom side of the top plate 1 and a driving wheel 26 fixed to the shaft 27. The gear box 28 comprises bearings to sustain the shaft 27 and passes the driving thrust to the sensor plate 9 to which it is mounted. To keep the load on the sensor plate 9 small, it is useful to put a load sensor 8 beneath the sensor plate 9, to which the gear box is mounted and a nonslip foot 4 below the chassis 2, to which the load sensor 8 is mounted. The motor 12 drives the hypoid or bevel gear via a coupling 11. The gear box 28 comprises such a large turning resistance, that the load by the person cannot turn the turntable by its own force. Thus, accidents are avoided, when a person steps on or off the top plate 1.

A deep groove ball thrust bearing or roller thrust bearing supports the top plate 1 in vertical direction and to some extent also in horizontal direction. The upper guiding ring of the thrust bearing 29 is mounted directly to the top plate 1, and because of its bending stiffness it also reduces the required thickness of the top plate 1. The lower guiding ring of the thrust bearing 30 forms a rigid rest for the cage with balls or rollers 31 and distributes the vertical load to the circular arranged load cells below the sensor plate, to which the lower guiding ring is mounted.

The axle 32 in the center of the turntable only serves as a fixture of the turntable and is secured with a retaining ring.

Figure 6A:
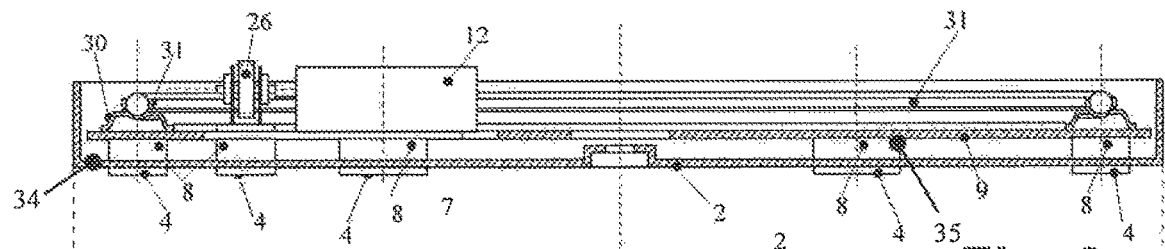
FIG. 6a is a cross-sectional view and FIG. 6b is a top plan view of an alternate embodiment of the turntable with removed top plate and frame.
Figure 6B:
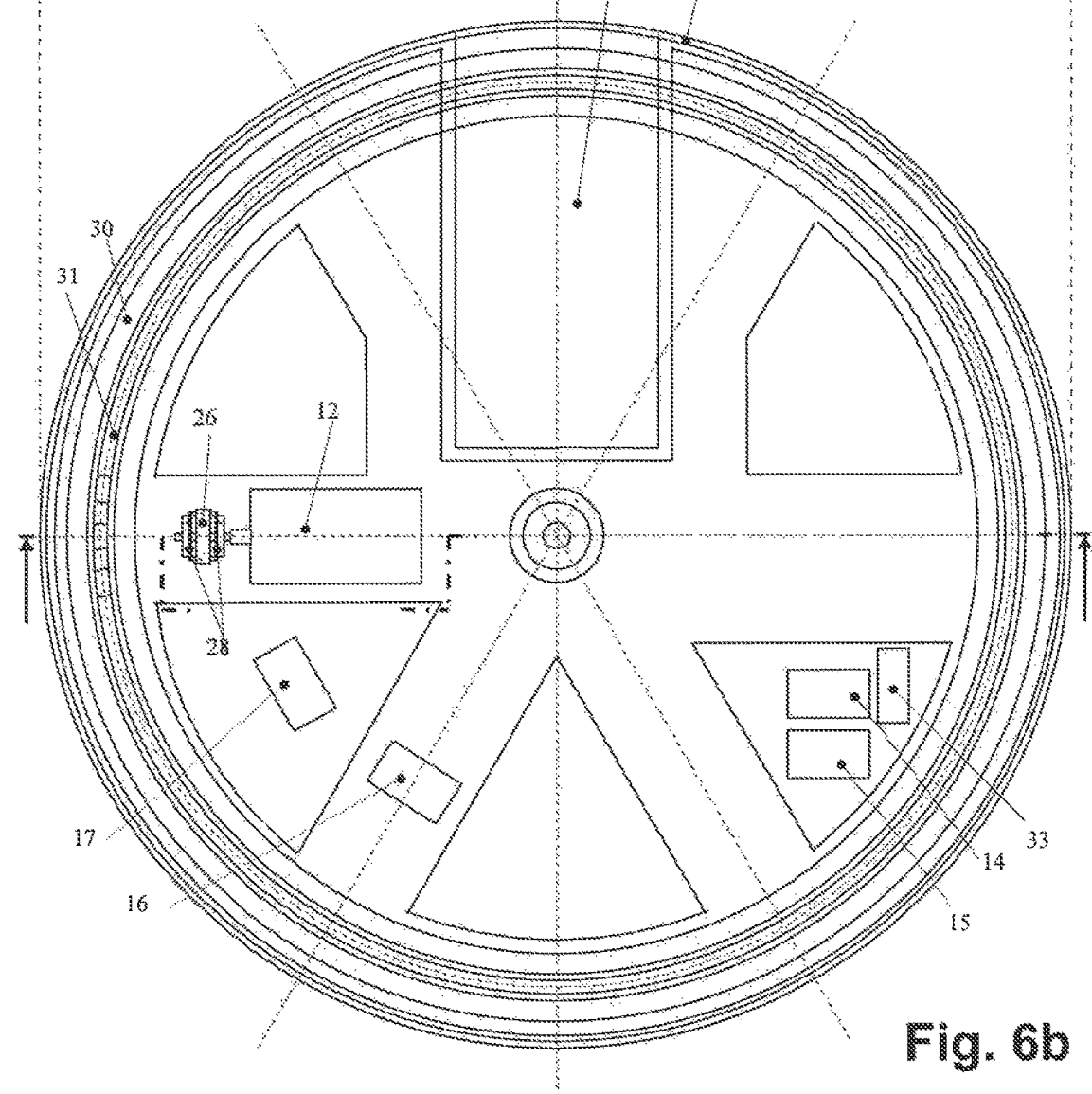

FIG. 6*a* is a cross-sectional view and FIG. 6*b* is a top plan view of an alternate embodiment of the turntable with removed top plate. A single sensor plate 9 rests solely on load cells 8 that are fixed to the chassis 2. Outside at the bottom of the chassis 2, nonslip feet 4 are attached, so that every load cell 8 rests above a nonslip foot 4. While most of the loadcells 8 are arranged periodically in a circle below the thrust bearing, i.e. cage with balls or rollers 31, and lower bearing ring 30, motor 12 and housing of the driving hypoid or bevel gear 28 might be supported by its own loadcells and nonslip feet to avoid bending stress in the sensor plate 9. Of course, a split of the sensor plate 9 into several partial plates is possible in this alternate design as well.

Locations of magnetic 16 and optical 17 position detection units shall be at different radii to the central axis from the position of the driving wheel. Electronic module 14 and power supply unit 15, in particular the rechargeable battery, may be located anywhere within the chassis 2. The height of the module plug-in 13 is restricted to the headroom below the lower bearing ring. However, due to the fact that the module plug-in will not support the thrust bearing, the support plates of the lower bearing ring might have a cut-out above the module location.

The motor driven turntable with integrated electronic scale 35 includes one or more of the following features:

(a) a rigid, motor driven top plate 1, withstanding the weight of a person standing or an object lying on the turntable, with a driving shaft mounted to the bottom side, whereby the directions of the symmetry axes of top plate and shaft are coincident;

(b) a chassis 2 acting as bottom plate 34 and lower part of the housing comprising:

load cells 8 firmly mounted to the bottom plate 34 within the chassis 2, (ii) at least one sensor plate 9, resting on and fixed to load cells 8, so that each of the sensor plates 9 is firmly connected to but not in touch with the chassis 2, (iii) vertical supporting rollers, resting in a guideway or fixed on a sensor plate 9, so that the position of the pitch points of the wheels touching the top plate 1 is exactly above the load cells 8, respectively, so that the direction of the flux of force is exactly vertical and no bending moment applies to the sensor plates 9, (iv) a gear, mounted to a sensor plate 9, to apply the driving torque to the driving shaft of the top plate 1, comprising driving and driven wheels as well as bearings for supporting vertical and horizontal load as applied from the top plate 1 if the turntable is not standing exactly leveled, and to support the top plate 1 in the center, (v) a motor, mounted to a sensor plate 9, to provide the driving torque to the gear, (vi) electronic circuitry for interpreting and analyzing data of scale sensors and for control of the motor, and (vii) a power supply unit, in particular a rechargeable battery, to provide electrical power for motor and electronic circuitry; and (c) nonslip feet 4 on the bottom side of the chassis 2 below each load cell 8 and in the axis of the flux of force.

Additionally or alternatively, the motor driven turntable with integrated electronic scale 35 comprises one or more of the preceding or following features:

(a) a rigid, motor driven top plate, withstanding the weight of a person standing, or an object lying, on the turntable, with an axle on the bottom side, whereby the directions of the symmetry axes of top plate and axle are coincident;

(ii) a toothed ring acting as driven wheel of the driving bevel gear, whereby the directions of the symmetry axes of top plate and the toothed ring are coincident;

(b) a chassis 2 acting as bottom plate 34 and lower part of the housing comprising:

at least three load cells firmly mounted to the bottom plate 34 within the chassis 2, (ii) at least one sensor plate, resting on and fixed to load cells, so that each of the sensor plates is firmly connected to but not in touch with the chassis 2, (iii) a thrust bearing fixed on at least one sensor plate and resting above at least three load cells that carries the top plate, (iv) a hypoid or bevel gear, to apply the driving torque to the toothed ring, fixed to the top plate, wherein the housing of the driving wheel is mounted to a sensor plate, (v) a motor, mounted to a sensor plate, to provide the driving torque to the gear, (vi) electronic circuitry for interpreting and analyzing sensor data and for control of the motor, and (vii) a power supply unit, in particular a rechargeable battery, to provide electrical power for motor and electronic circuitry; and (c) nonslip feet on the bottom side of the chassis below each load cell and in the axis of the flux of force.

Additionally or alternatively, the motor driven turntable comprises two or more additional load cells 8 between chassis 2 and sensor plate 9 and a corresponding number of nonslip feet 4 at the bottom side of the chassis 2, located below the housing of the gear, to allow a vertical flux of force from gearbox to the floor.

Additionally or alternatively, the sensor plate has cut-outs to allow mounting of any modules and subassemblies directly to the bottom plate 34 of the chassis 2.

Additionally or alternatively, the motor driven turntable comprises a ring-shaped frame 3 with attached skirt of cylindrical or conical shape, mounted inside to the chassis 2 or to the top plate 1, cladding the gap between chassis 2 and top table to reduce intrusion of dust into the body of the turntable.

Additionally or alternatively, the motor driven turntable comprises at least one pair of pillars 23 for routing cables 22 horizontally from subassemblies located on the sensorplate 9 to subassemblies mounted to the chassis 2, with one pillar 23 fixed on the sensorplate 9, the other one fixed on the chassis 2, both pillars 23 with a mechanism for fixation of a cable 22 at the same height above the chassis 2.

Additionally or alternatively, the top plate 1 carries an optical scale or markings that allow the finding of the angular position of the top plate; and in which an optical sensor is included, to read the optical scale or markings from the top plate.

Additionally or alternatively, the top plate 1 carries a magnetic scale or single magnets that allow the finding of the angular position of the top plate. Additionally or alternatively, a magnetic sensor is equipped to read the magnetic scale or positions of magnets from the top plate.

The electronic circuitry also comprises an interface 33 for a connection to at least one external computer.

The motor driven turntable according to the previous specification is used in an arrangement for fitness monitoring, personal biofeedback and/or medical diagnostic of a person. The arrangement comprises an apparatus for optical measurement of a body of the inspected person. The apparatus comprises the "external" computer. In a preferred embodiment the apparatus is a 3D body scanner and/or comprises at least one color camera, depth sensor and/or far infrared temperature sensor. The motor driven turntable is used to turn the person during the 3D body scan. Therefore, the computer of the 3D body scanner comprises a second wireless interface, which is wirelessly connected to the first wireless interface of the motor driven turntable. Thus, the motor driven turntable can be controlled by the computer of the apparatus. Furthermore, data captured from the sensors of the motor driven turntable can be sent to the computer.

LIST OF REFERENCE CHARACTERS 1 top plate
2 chassis
3 ring-shaped frame
4 nonslip feet
5 vertical supports
6 roller of vertical support/support roller
7 vertical guideway
8 load cells
9 sensor plate
10 gear
11 coupling
12 motor
13 module plug-in
14 electronic module
15 power supply unit
16 magnetic position detection unit
17 optical position detection unit
18 main shaft
19 radial ball bearing
20 axial roller bearing
21 spacer washer
22 cable
23 pillar
24 fixing for cable
25 toothed ring (of the bevel gear)
26 driving wheel (of the bevel gear)
27 shaft (of the bevel gear)
28 gear box
29 upper bearing ring
30 lower bearing ring
31 cage with balls or rollers
32 axle
33 wireless interface
34 bottom plate
35 integrated electronic scale

The invention claimed is:

1. Motor driven turntable for at least one of a fitness monitoring, personal biofeedback and medical diagnostic apparatus having an external computer, the motor driven turntable comprising:
   a bottom plate,
   a top plate rotatably connected to the bottom plate,
   a motor connected for rotatably driving the top plate,
   an integrated electronic scale for measuring the weight of a person positioned on the top plate and
   a wireless interface connected to the integrated electronic scale and configured to permit the integrated electronic scale to communicate with the external computer of the fitness monitoring, personal biofeedback and medical diagnostic apparatus;
   a position detection unit carried by the bottom plate and configured for measurement of an angular position of the top plate; and
   a microprocessor connected to the integrated electronic scale and configured to acquire data from the integrated electronic scale;
   wherein the wireless interface is configured to provide the acquired data from the microprocessor to the external computer;
   wherein the wireless interface is configured to provide the acquired data from the microprocessor to supply data of the angular position of the top plate to the external computer;
   wherein the wireless interface is configured to provide the acquired data from the microprocessor to supply data of the person's weight to the external computer; and
   wherein the wireless interface is configured to allow the external computer to control the motor.

2. A motor driven turntable according to claim 1, wherein the wireless interface is a WLAN, WIFI, Zigbee or Bluetooth interface.

3. A motor driven turntable according to claim 1, wherein the position detection unit comprises an optical sensor and/or a magnetic sensor.

4. A motor driven turntable according to claim 1, wherein the microprocessor is configured for interpreting and analyzing data of the integrated electronic scale and of the optical and/or magnetic sensor, and wherein the microprocessor is configured for control of the motor.

5. A motor driven turntable according to claim 1, further comprising a power supply unit that includes a rechargeable battery, to provide electrical power for the motor and the microprocessor.

6. An arrangement for fitness monitoring, personal biofeedback or medical diagnostic of an inspected person, the arrangement comprising:
   an external computer;
   an apparatus configured for optical measurement of a body of the inspected person with the external computer, wherein the apparatus is a 3D body scanner and/or includes a color camera, a depth sensor or a far infrared temperature sensor;
   a motor driven turntable according to claim 1; and
   a first wireless interface configured to communicate with the external computer of the apparatus; and wherein the 3D body scanner includes a color camera, a depth sensor or a far infrared temperature sensor.

7. Arrangement for fitness monitoring, personal biofeedback or medical diagnostic of an inspected person, the arrangement comprising:
- an external computer;
- an apparatus configured for optical measurement of a body of the inspected person, wherein the apparatus is a 3D body scanner that includes the external computer;
- a motor driven turntable including a bottom plate, a top plate rotatably connected to the bottom plate, a motor connected for rotatably driving the top plate, an integrated electronic scale for measuring the weight of a person positioned on the top plate;
- a first wireless interface connected to the integrated electronic scale and configured to permit the integrated electronic scale to communicate with the external computer of the apparatus; and
- a position detection unit carried by the bottom plate and configured for measurement of an angular position of the top plate;
- wherein the external computer includes a second wireless interface, which is wirelessly connected to the first wireless interface so that the external computer is able to control the motor of the motor driven turnable; and
- wherein the external computer includes a third wireless interface configured for connecting the external computer to a smartphone.

8. An arrangement according to claim 7, wherein the apparatus is a 3D body scanner and/or comprises a color camera, a depth sensor or a far infrared temperature sensor.

* * * * *